(12) United States Patent
Thomann et al.

(10) Patent No.: US 10,858,691 B2
(45) Date of Patent: Dec. 8, 2020

(54) DIFFERENTIAL SHEARING OF NUCLEIC ACIDS

(71) Applicant: Covaris, Inc., Woburn, MA (US)

(72) Inventors: Hans-Ulrich Thomann, Stow, MA (US); James A. Laugharn, Jr., Boston, MA (US)

(73) Assignee: Covaris, Inc., Woburn, MA (US)

( * ) Notice: Subject to any disclaimer, the term of this patent is extended or adjusted under 35 U.S.C. 154(b) by 256 days.

(21) Appl. No.: 15/954,971

(22) Filed: Apr. 17, 2018

(65) Prior Publication Data
US 2018/0298425 A1 Oct. 18, 2018

Related U.S. Application Data

(60) Provisional application No. 62/486,615, filed on Apr. 18, 2017.

(51) Int. Cl.
| | | |
|---|---|---|
| *C12Q 1/6806* | (2018.01) | |
| *C12N 15/10* | (2006.01) | |
| *C12Q 1/6869* | (2018.01) | |

(52) U.S. Cl.
CPC ....... *C12Q 1/6806* (2013.01); *C12N 15/1003* (2013.01); *C12Q 1/6869* (2013.01)

(58) Field of Classification Search
CPC .................................................. C12Q 1/6806
USPC ........................................................ 506/16
See application file for complete search history.

(56) References Cited

U.S. PATENT DOCUMENTS

| | | | |
|---|---|---|---|
| 9,982,290 B2 * | 5/2018 | Janzen | .................. C12N 15/10 |
| 2014/0274740 A1 | 9/2014 | Srinivasan et al. | |
| 2016/0348152 A1 * | 12/2016 | Zheng | .................. C12Q 1/6806 |

FOREIGN PATENT DOCUMENTS

| | | |
|---|---|---|
| WO | WO 2016/176131 A1 | 11/2016 |
| WO | WO 2017/027835 A1 | 2/2017 |
| WO | WO 2017/173039 A1 | 10/2017 |

OTHER PUBLICATIONS

Bronkhorst et al. (Biomolecular Detection and Quantification 17, 2019, pp. 1-23) (Year: 2019).*
Metcalf et al. (Clinical Microbiology and Infection, 22, 2016, pp. 1002.e1-1002.e8). (Year: 2016).*
International Preliminary Report on Patentability for International Application No. PCT/US2018/028092, dated Oct. 31, 2019.
International Search Report and Written Opinion for International Application No. PCT/US2018/028092, dated Jun. 27, 2018.
Karami et al. Introducing a new and simple protocol for capillary electrophoresis of cell free fetal double stranded DNA. Journal of Sciences, Islamic Republic of Iran. Jan. 1, 2014;25(4):305-308.
Shu et al., Circulating tumor DNA mutation profiling by targeted next generation sequencing provides guidance for personalized treatments in multiple cancer types. Scientific Reports. Apr. 3, 2017;7(1):1-11.

* cited by examiner

*Primary Examiner* — Karla A Dines
(74) *Attorney, Agent, or Firm* — Wolf, Greenfield & Sacks, P.C.

(57) ABSTRACT

Focused acoustic treatment of samples may be used to differentially shear different fragment lengths of DNA or other nucleic acid portions of a sample. Relatively larger fragment lengths may be sheared while smaller fragment lengths are unaffected by the focused acoustic based shearing.

16 Claims, 8 Drawing Sheets

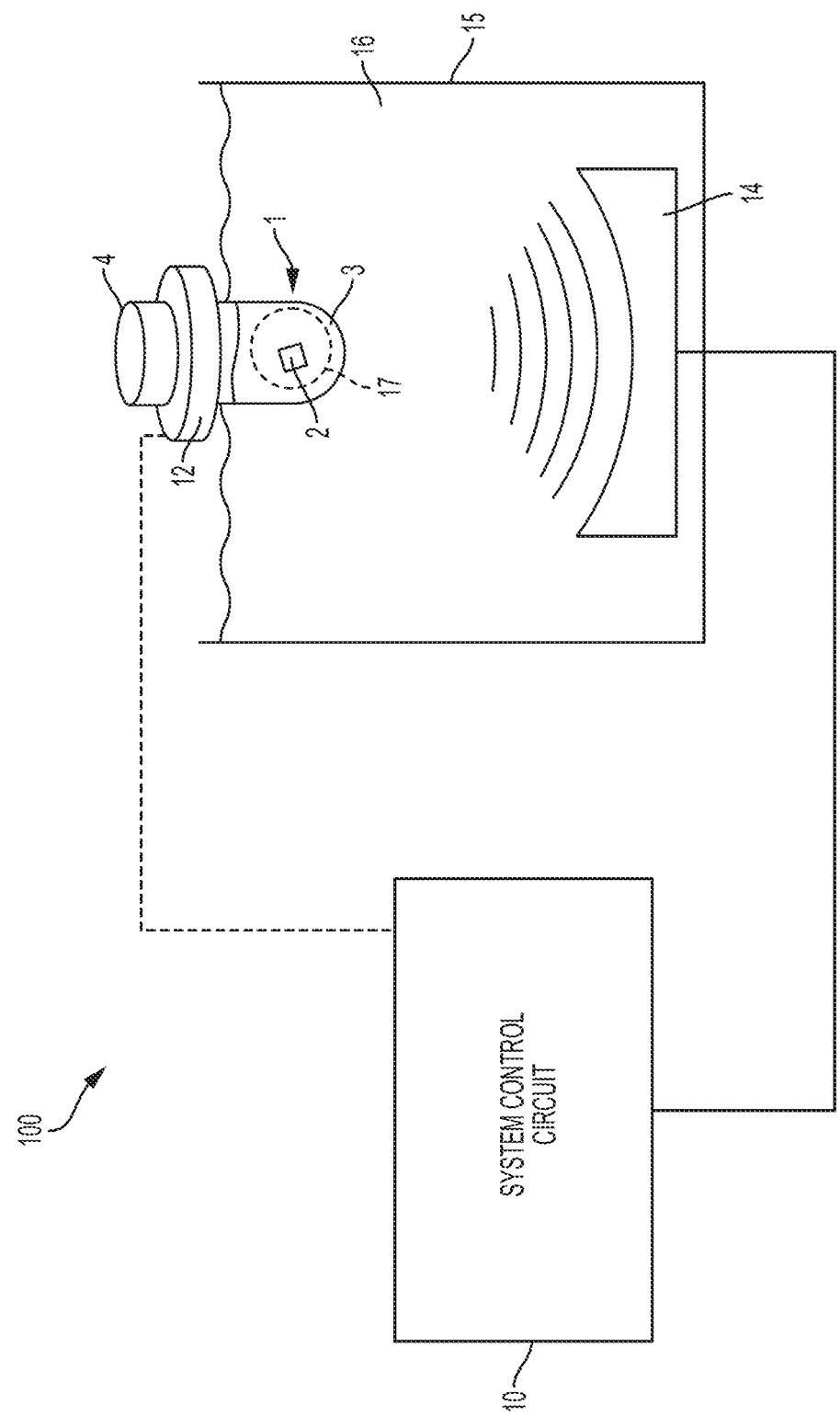

DIFFERENTIAL SHEARING OF NUCLEIC ACIDS

RELATED APPLICATION

This Application claims priority under 35 U.S.C. § 119(e) to U.S. Provisional Application Ser. No. 62/486,615, entitled "DIFFERENTIAL SHEARING OF NUCLEIC ACIDS" filed Apr. 18, 2017, which is herein incorporated by reference in its entirety.

BACKGROUND

1. Field of the Invention

Systems and methods for processing of samples with acoustic energy are generally disclosed.

2. Related Art

Acoustic energy-based sample processing devices, such as Adaptive Focused Acoustic (AFA) apparatuses made by Covaris of Woburn, Mass., are effective for homogenization and disruption of biological tissues, cells, and other sample material. With such devices, a controlled acoustic field enables repeatable processes to be developed which often result in higher recovery of target molecules as compared to bath and probe sonicators, blade homogenizers, and bead beaters. Such target molecules may be, for example, DNA, RNA, or proteins.

SUMMARY OF INVENTION

Controlled fragmentation of high molecular weight DNA is a pre-requisite for next generation sequencing (NGS) technologies. After isolation and purification of high molecular weight DNA which is usually larger than 10 kbp in average length, the DNA is fragmented to a desired average fragment length so that it can be used as substrate or library for NGS analysis. As an example, typical required size ranges for DNA fragments for use with Illumina-based sequencing processes are between 150 and 500 bp. In some cases, NGS processes use DNA polymerase-based incorporation of deoxynucleotides to extend a primer and synthesize a strand that is complementary to the template, similar to Sanger sequencing. In each successive cycle of sequencing, a nucleotide is incorporated which generates a chemical (pH change) or optical (fluorescence) signal. In the case of optical detection, a signal generated by fluorescently labeled nucleotides (dNTPs) and is read out after each cycle. The modified dNTPs do not terminate the chain, but can be extended for continuing sequencing cycles. In a massively parallel fashion, millions of DNA fragments can be read at the same time.

Since many NGS processes are capable of simultaneously analyzing millions of DNA fragments together in a single run, combining DNA fragments from different sources in a single sequencing run (known as multiplexing DNA fragment pools) can provide for more efficient use of resources and time. However, multiplexing of DNA fragment pools requires that the DNA fragments from the different pools be indexed or tagged so that the DNA fragments and their sequencing results can be properly correlated with the appropriate pool For example, indices (also known as tags or barcodes) are required if a NGS run involves the parallel analysis of DNA fragments from discrete starting samples, such as samples derived from a human and a microbial specimen. The indices identify different starting samples from each other, allowing for samples from different sources to be sequenced together and sequencing results to be correlated to corresponding samples. Pool multiplexing and the use of indices is especially useful if the individual pool libraries to be sequenced either do not require deep sequence coverage (i.e., redundant coverage of the fragment population that is present in the same library) or the fragment number that is needed to redundantly cover a genome is too low to fill all the available spots in a NGS chip. The latter is true for most microbial genomes that are a fraction in size (0.5 to 100 Mbp) as compared to those of higher eukaryotes (>100 to 5,000 Mbp).

For multiplexed pool sequencing when more than one library is run in the same flow cell, short double stranded DNA molecules with a known sequence of 6 to 8 nucleotides can be used as indices (tags or barcodes), and can be ligated to the library DNA fragments before the different pool fragments are combined together. During the sequencing run, the index sequence is read first and is used during data analysis of a multiplexed run to identify each library, i.e., to associate the sequencing results with the corresponding source of the DNA fragments. Such indexing or tagging is limited, however, by the number of tags available. Most commercial kits offer less than 50 different tags, but in principle the number of possible tags is only limited by the number of possible basepair combinations. That is, since tags are made of 6 possible bases, tags can theoretically be produced having $4^6$ (4096) different tag sequence variations. However, in practice the total available number of tags is limited by natural attrition due adverse impacts of certain sequence combinations, such as strong secondary structures (hairpin formations) and melting temperatures that are incompatible with downstream processing, such as PCR, hybridization and annealing of probes. As a result, the total number of practically usable tags is much less than the 4096 base pair theoretical limit. Moreover, while multiplexing DNA fragment pools can provide throughput advantages, multiplexing pools typically involves the combination of DNA fragments from different pools that were sheared to identical or very similar average fragment base pair lengths, and the fragment sizes are typically quite small. Therefore, the number of pools that can be multiplexed may be limited by the number of DNA fragments from each sample, since there is a practical limit to the number of tags that can be used to uniquely identify the fragments.

In accordance with an aspect of the invention, two or more pools of DNA fragments, whether obtained from a same or different sources, may be multiplexed without using tags or other fragment identifiers, and yet sequencing results for the different DNA fragment pools may be appropriately corresponded with the corresponding pool. In one embodiment, two or more DNA fragment populations or sets of DNA fragments may be mixed or otherwise combined together, e.g., for NGS processing. The DNA fragments from the respective pools or sets may differ from each other in their fragment size distribution, and this difference in fragment size may be used to correspond sequencing results with the appropriate set of DNA fragments. Thus, the use of tags may be eliminated entirely, or if used, the tags need not be used to identify fragments as belonging to a particular set of DNA fragments. That is, tags may be used to identify DNA fragments for some purpose, such as having a particular base pair sequence, but need not be used to identify DNA fragments as belonging to a particular set of DNA fragments. In one example, a multiplexed pool of DNA fragments may include a first set of DNA fragments including native cell free DNA (cfDNA), e.g., having nucleosomal fragments with a base pair size of less than 180 bp. The multiplexed pool may also include a second set of DNA fragments including other, larger DNA fragments, such as having a size of 300-500 bp. As noted above, the base pair sizes for the first and second sets of DNA fragments are suitable for NGS processing, and DNA fragments from both the first and second sets may be sequenced together, at the same time. Sequencing results for the first and second sets of DNA fragments may be properly correlated with the corresponding set of fragments based on the base pair length of the sequenced fragment. Fragments having a length less than 180 bp belong to the first set, whereas fragments having a longer length belong to the second set. Multiple sets of DNA fragments may be multiplexed together as well, and sequencing results determined based on fragment length. For example, a first set may have a fragment size under 180 bp, a second set may have a fragment size between 180 bp and 300 bp, and a third set may have a fragment size of greater than 300 bp. Sequencing results may be correlated with the proper set of DNA fragments based on fragment length.

In another aspect of the invention, two or more sets of DNA fragments (or other nucleic acid portions) may be combined together, and one of the sets sheared so as to reduce the length of the DNA fragments in the set while DNA fragments in the other set(s) are not sheared. Such a technique may be particularly useful, for example, where the two or more sets of nucleic acid portions are obtained from a same source (such as a blood sample from a human) and at least one of the sets of nucleic acid portions needs to be reduced in fragment size for NGS processing. One example may be a blood sample, which includes nucleosomal cfDNA, which has a maximum size of 180 bp or 340 bp, and other heavier molecular weight cfDNA which may be of somatic origin (i.e., DNA set free from lysed or necrotic cells), having a base pair size of greater than 1000 bp. The heavier molecular weight cfDNA may need to be sheared for at least some NGS processes, e.g., to fragments having a maximum size of 500 bp or less. In one embodiment, the heavier molecular weight cfDNA may be sheared to the desired base pair length of 500 bp or less while mixed with the nucleosomal cfDNA and without having any shearing effect on the nucleosomal cfDNA. This may allow for a variety of advantages, such as eliminating any need to separate the nucleosomal cfDNA and other cfDNA, such as higher molecular DNA of somatic origin, to allow for shearing of the larger cfDNA, reducing the chance of contamination of the samples (e.g., due to separation, treatment in separate vessels, and then recombination of the cfDNA after shearing), allowing for shearing of the nucleosomal cfDNA and larger cfDNA in a same vessel in which the samples were harvested, and so on.

In one aspect of the invention, a method for shearing selected nucleic acid portions of a sample includes providing a sample in a vessel containing a first set of nucleic acid portions having a first base pair length and a second set of nucleic acid portions having a second base pair length, where the second base pair length is larger than the first base pair length. The sample in the vessel may be exposed to focused acoustic energy to selectively shear only the second set of nucleic acid portions to produce a third set of nucleic acid portions having a third base pair length that is less than the second base pair length but greater than the first base pair length. However, the focused acoustic energy does not shear the first set of nucleic acid portions. In some embodiments, a total energy of the acoustic energy used to treat the sample is selected to shear the second set of nucleic acid portions to a desired third base pair length, but yet not shear the first set of nucleic acid portions.

In one embodiment, the sample includes blood having nucleosomal cfDNA comprising the first set of nucleic acid portions and larger base pair length cfDNA comprising the second set of nucleic acid portions. In some cases, the larger base pair length cfDNA is apoptotic or necrotic in origin. The nucleosomal cfDNA may have a base pair length of less than 180 bp, and the larger base pair length cfDNA may have a base pair length greater than 1000 bp. In other cases, the nucleosomal cfDNA may have a base pair length of less than 400 bp, and the larger base pair length cfDNA may have a base pair length greater than 500 bp. After acoustic energy treatment, the third set of nucleic acid portions may include sheared fragments of the larger base pair length cfDNA, wherein the sheared fragments have a base pair length of about 300-500 bp. This may allow for NGS analysis of the first and third sets of nucleic acid portions, e.g., the method may include simultaneously using the first and third sets of nucleic acid portions together in a library of a next generation sequencing (NGS) process. Alternately, the first and third sets may be used for other purposes, e.g., the first and third sets of nucleic acid portions may be separated by gel electrophoresis, size-selective binding and elution or gel filtration.

As discussed above, the total energy of the focused acoustic energy may control the size to which the second set of nucleic acid portions are sheared, and increasing total energy of the acoustic energy may correspond to smaller fragment sizes for the third set of nucleic acid portions. In some cases, the focused acoustic energy has a duty cycle of 50% or less, and a peak incident power (PIP) of 20 W to 200 W. A time of acoustic energy treatment may be adjusted to adjust a total energy of the treatment, although adjustments to the duty cycle and/or peak incident power may be made as well. In some embodiments, the focused acoustic energy is generated by an acoustic energy source spaced from and exterior to the vessel, and the focused acoustic energy comprises a frequency of between about 100 kilohertz and about 100 megahertz and a focal zone having a width of less than about 2 centimeters. The acoustic energy source may include an acoustic transducer having a dome shape and arranged to generate focused acoustic energy to create the focal zone, and the sample may have a volume of 10 microliters to 150 milliliters.

In another embodiment, a method for shearing selected nucleic acid portions of a sample includes providing a sample in a vessel containing a first set of nucleic acid portions each having a base pair length less than a threshold and a second set of nucleic acid portions each having a base pair length greater than the threshold. The sample in the vessel may be exposed to focused acoustic energy to selectively shear only the second set of nucleic acid portions to produce a third set of nucleic acid portions having a base pair length that is less than the base pair length of the second set of nucleic acid portions but greater than the base pair length of the first set of nucleic acid portions. The focused acoustic energy will not, however, shear the first set of nucleic acid portions.

In another embodiment, a method for shearing selected nucleic acid portions of a sample includes providing a sample in a vessel containing a first set of nucleic acid portions including supercoiled DNA having a first base pair length and a second set of nucleic acid portions including linear DNA having a second base pair length. In some cases, the first and second base pair lengths may be the same or similar, or different. The sample in the vessel may be exposed to focused acoustic energy to selectively shear only the second set of nucleic acid portions to produce a third set of nucleic acid portions having a base pair length that is less than the second base pair length of the second set of nucleic acid portions, but the focused acoustic energy does not shear the first set of nucleic acid portions.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein:

FIG. 8 shows a schematic block diagram of an acoustic treatment system that may be used to provide focused acoustic treatment in one or more embodiments.

DETAILED DESCRIPTION

Figure 1:
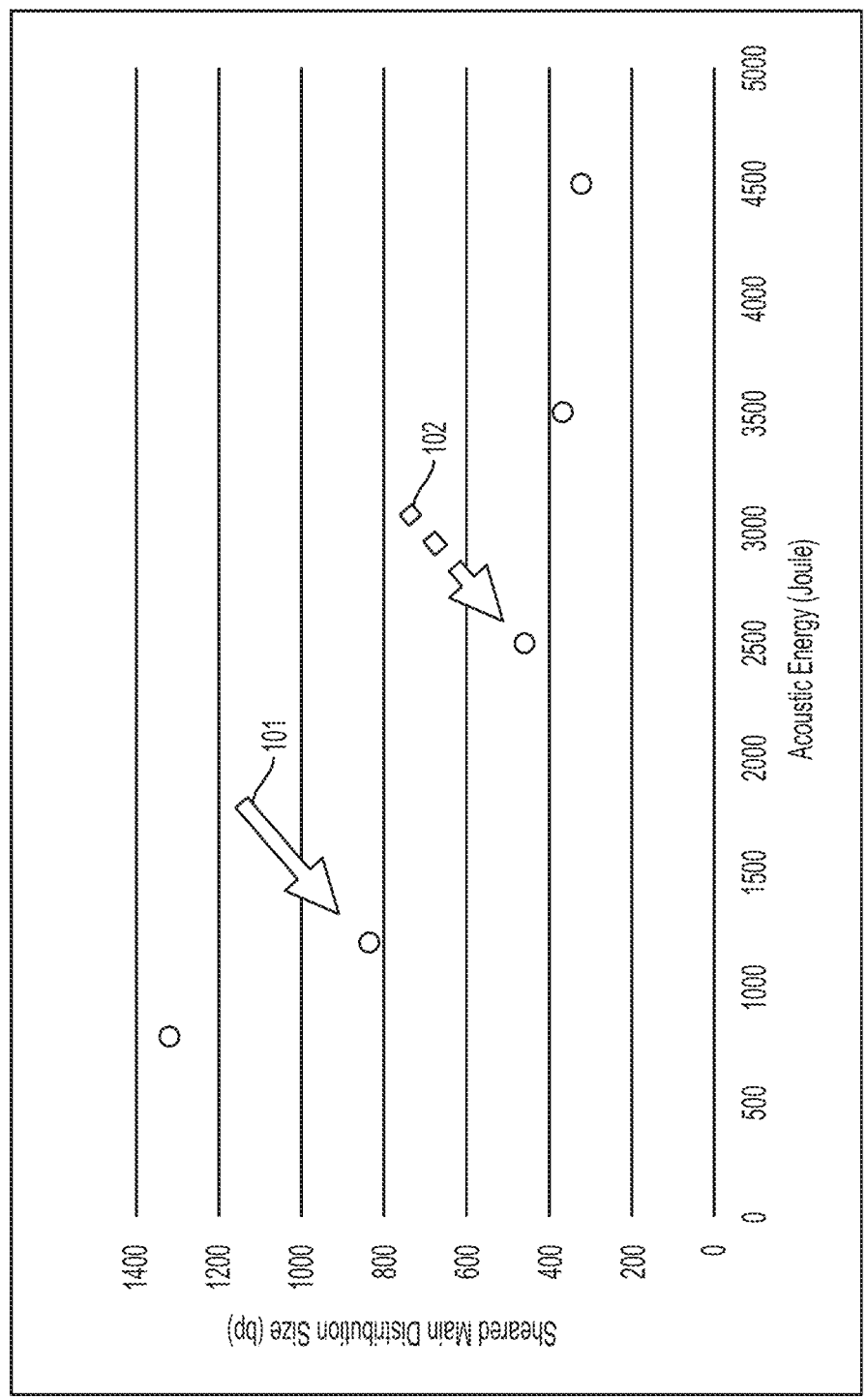
FIG. 1 shows corresponding minimum fragment sizes for different total energy inputs of focused acoustic energy in one embodiment.

Aspects of the invention are not limited in application to the details of construction and the arrangement of components set forth in the following description or illustrated in the drawings. Other embodiments may be employed and aspects of the inventions may be practiced or be carried out in various ways. Also, the phraseology and terminology used herein is for the purpose of description and should not be regarded as limiting.

As described above, aspects of the invention provide for the ability to shear DNA fragments or other nucleic acid portions of one set without shearing DNA fragments or other nucleic acid portions of another set while the sets of nucleic acid portions are combined together. To illustrate embodiments in which two different sets of nucleic acid portions may be combined together, and one of the sets sheared while the other set is not sheared, several examples involving experiments performed are discussed in detail below. The inventors have discovered that a total energy of focused acoustic energy used to treat a sample including DNA fragments or other nucleic acid portions correlates with a minimum fragment size that the focused acoustic energy will shear. That is, for a given total energy of focused acoustic energy, DNA fragments or other nucleic acid portions over a particular base pair length will be sheared, while DNA fragments or other nucleic acid portions are not. (For brevity, descriptions herein may refer only to DNA fragments, but it should be understood that other nucleic acid portions may be used as well, such as RNA or other nucleic acid constructs.) FIG. 1 shows a plot of focused acoustic energy levels used for shearing DNA fragments against the resulting sheared DNA fragment size in one experiment. In this example (described in more detail below), relatively high weight lambda DNA (having a base pair length of about 48 kbp) was sheared using different total acoustic energy levels. The lambda DNA was sheared using a Covaris E220 focused ultrasonicator at different total energy levels (measured in Joules), and it was found that the lambda DNA was sheared to a minimum base pair length that corresponds to the total input energy level. For example, as shown by the arrow 101 in FIG. 1, a total energy level of 1200 Joules resulted in shearing to fragments having an average base pair length of about 800 bp. However, as shown by the arrow 102 in FIG. 1, a total energy level of 2500 Joules resulted in shearing to fragments having an average base pair length of about 450 bp. As described in more detail below, it has been surprisingly found that DNA fragments having a size below the corresponding minimum base pair length for a total input energy level are not sheared by focused acoustic energy at that total energy level. For example, focused acoustic energy at a total energy level of 1200 Joules would not shear DNA fragments having a size below 800 bp. Thus, if such DNA fragments were present in the sample treated with the focused acoustic energy, those DNA fragments would be unaffected while larger DNA would be sheared. The inventors have realized that this input energy dependency can be utilized to differentially shear relatively larger DNA fragments to a smaller target size without impacting relatively smaller DNA fragments that are present in the same sample. So, while the specific total input energy and corresponding sheared fragment size may vary for different samples, the general relationship that increasing input energy will shear fragments to smaller base pair lengths while not shearing fragments below the minimum base pair length for the input energy can be used to shear relatively larger fragments to smaller size without affecting relatively smaller fragments in a sample.

In the experiments performed to generate the results in FIG. 1 (referred to as Example 1), bacteriophage Lambda DNA (P/N N3011S; NEB, Ipswich, Mass.) was diluted to 2 ng/μl in Tris-EDTA (TE) buffer and was sheared at different energy settings in a Covaris milliTUBE-1 ml in a Covaris E220 focused-ultrasonicator. 1 μl of the resulting sheared DNA was analyzed on a BioAnalyzer chip (12000 kit P/N 5067-1508; Agilent Technologies, Santa Clara, Calif.) and the mean resulting DNA fragment size recorded. As can be seen in FIG. 1, a total focused acoustic energy of about 750 Joules sheared the Lambda DNA to a mean fragment size of about 1350 bp. This total energy level would not, however, shear fragments in the sample that were below about 1350 bp. Similar was true for treatment of the samples at 1200 and 2500 Joules, as discussed above. Samples were also treated with total energy of about 3500 Joules and 4500 Joules, which respectively sheared the Lambda DNA to mean fragment sizes of about 375 bp and 325 bp. As in the other acoustic energy treatment experiments, however, fragments below the mean fragment size corresponding to the total energy level were not sheared by the acoustic energy. In these experiments, the total energy (E) applied to a sample via acoustic energy is measured in Joules and given by the product of peak incident power of the focused acoustic energy (PIP in Watts) by the duty cycle of the focused acoustic energy (DC in percentage terms) by the total processing time (T in seconds) or E=PIP*DC*T.

As detailed more below, the inventors' appreciation that discrete total energy levels result in shearing to defined fragment sizes may be applied to differentially shear two fragment populations present in a same sample. For example, if a DNA fragment population of 450 bp mean fragment size were spiked into (or mixed with) a high molecular weight fragment pool (such as 2.99 kb DNA) and a total energy of 1200 Joules of focused acoustic energy is applied to the mixed sample according to the conditions of Example 1, the 2.99 kb DNA pool will be sheared to a mean fragment size distribution of about 800 bp. In contrast, the 450 bp fragment pool in the sample will not be impacted, as the total energy is too low for shearing this fragment size. Hence, only one fragment size pool, i.e., the 2.99 kb pool, will be sheared, and the lower molecular weight pool of 450 bp will not change in mean fragment size. In order to shear DNA of 450 bp to a smaller size, energy in excess of 2500 Joules would be required according to FIG. 1.

One application for differential shearing features that can be employed with focused acoustic energy relates to sequencing cfDNA in blood and other samples. Such samples include relatively short, nucleosomal cfDNA fragments as well as higher weight cfDNA fragments. While current analysis tends to focus on short cfDNA fragments, often because of difficulties in analyzing higher weight cfDNA fragments, assessment of the higher weight cfDNA fragments may have value, and aspects of the invention provide improved techniques for assessing both nucleosomal cfDNA and higher weight cfDNA, as an example. According to the current paradigm, short cfDNA fragments include fragments mostly corresponding to about 170 bp mono-nucleosomal and about 340 bp di-nucleosomal DNA [Jahr, S., et al., DNA fragments in the blood plasma of cancer patients: quantitations and evidence for their origin from apoptotic and necrotic cells. Cancer Res, 2001. 61(4): p. 1659-65; Ivanov, M., et al., Non-random fragmentation patterns in circulating cell-free DNA reflect epigenetic regulation. BMC Genomics, 2015. 16 Suppl 13: p. S1]. In cancer, circulating tumor DNA typically consists of these short nucleosomal fragments which are linked to apoptosis, and higher molecular weight fragments which are linked either to necrosis [Jahr, S., et al., DNA fragments in the blood plasma of cancer patients: quantitations and evidence for their origin from apoptotic and necrotic cells. Cancer Res, 2001. 61(4): p. 1659-65; Perez-Barrios, C., et al., Comparison of methods for circulating cell-free DNA isolation using blood from cancer patients: impact on biomarker testing. Transl Lung Cancer Res, 2016. 5(6): p. 665-672] or to exosomal origin [Gold, B., et al., Do circulating tumor cells, exosomes, and circulating tumor nucleic acids have clinical utility? A report of the association for molecular pathology. J Mol Diagn, 2015. 17(3): p. 209-24; Thakur, B. K., et al., Double-stranded DNA in exosomes: a novel biomarker in cancer detection. Cell Res, 2014. 24(6): p. 766-9]. This opens up new possibilities of early cancer detection by investigating the origin and mutations of the cancer as well as treatment response and clonal evolution [Yeh, P., et al., Circulating tumour DNA reflects treatment response and clonal evolution in chronic lymphocytic leukaemia. Nat Commun, 2017. 8: p. 14756]. As result, the circulating nucleosome fraction (small cfDNA) is valuable for clinically actionable mutation identification, therapy choice, and therapy monitoring since chemotherapy and targeted therapy release cfDNA due to apoptosis and is at the current focus of cfDNA assays [Schwarzenbach, H., D. S. Hoon, and K. Pantel, Cell-free nucleic acids as biomarkers in cancer patients. Nat Rev Cancer, 2011. 11(6): p. 426-3718; Holdenrieder, S., et al., Circulating nucleosomes predict the response to chemotherapy in patients with advanced non-small cell lung cancer. Clin Cancer Res, 2004. 10(18 Pt 1): p. 5981-7]. However, it is important that extraction and purification of cfDNA from plasma does not alter the natural fragment size distribution in the specimen since the ratio between nucleosomal (short) and long cfDNA is a promising biomarker for detection of breast cancers [Umetani, N., et al., Prediction of breast tumor progression by integrity of free circulating DNA in serum. J Clin Oncol, 2006. 24(26): p. 4270-6] and colorectal cancers [Hao, T. B., et al., Circulating cell-free DNA in serum as a biomarker for diagnosis and prognostic prediction of colorectal cancer. Br J Cancer, 2014. 111(8): p. 1482-9], as examples. Additionally, the ability to retrieve larger cfDNA fragments (greater than 1,000 bp) may be important for the investigation of non-apoptotic mechanisms. Furthermore, it is important to be able to determine the sequence content of the nucleosomal, low molecular weight cfDNA fraction as well as that from the high molecular weight cfDNA fraction, since they may be from different origins, different tissue and even cells with different pathology or disease stages.

However, presently, sequencing analysis is not possible without separating the two naturally occurring fractions in cfDNA preparations. Separating the two fractions during or after purification is cumbersome as the quantities of cfDNA in human plasma are low, usually 2-60 ng/mL plasma in healthy individuals. Jiang et al. (2015. Lengthening and shortening of plasma DNA in hepatocellular carcinoma patients. Proc Natl Acad Sci USA 112:E1317-E1325] have demonstrated this by a filtering method that captures DNA of a particular size range and the measuring fragment sizes by paired end sequencing. The method is not suited for fast analysis and is not adaptable to high throughput processing.

Thus, normally only the small cfDNA fragment sizes (nucleosomal fraction) are converted into linkerized library fragment pools and subsequently analyzable by NGS technologies. The larger fragments are usually not analyzed as they are too large for commercially available array-based NGS platforms, such as MiSeq (Illumina) or IonTorrent (ThermoFisher). Panel-based analysis that involves target capture based amplification and subsequent sequence analysis of selected loci, e.g., via the xGen Pan Cancer Panel (Integrated DNA Technologies, Coralville, Iowa) would not be able to distinguish between the two cfDNA fragment populations.

However, if the high molecular weight cfDNA fraction is fragmented to a shorter mean size pool, e.g., 300-500 bp, conversion into libraries and NGS analysis is possible. In accordance with aspects of the invention, shearing of the high molecular weight cfDNA fraction may be performed at energy levels that are sufficient to shear the high molecular weight cfDNA fraction to fragment sizes that are within the targeted 300-500 bp fragment size suitable for NGS analysis, and without any shearing of the nucleosomal cfDNA fragments present in the sample. Thus, aspects of the invention provide for the ability to shear relatively high molecular weight cfDNA portions of a sample to fragment sizes suitable for NGS analysis while mixed with, and with no impact on, a smaller nucleosomal cfDNA fraction.

Figure 2:
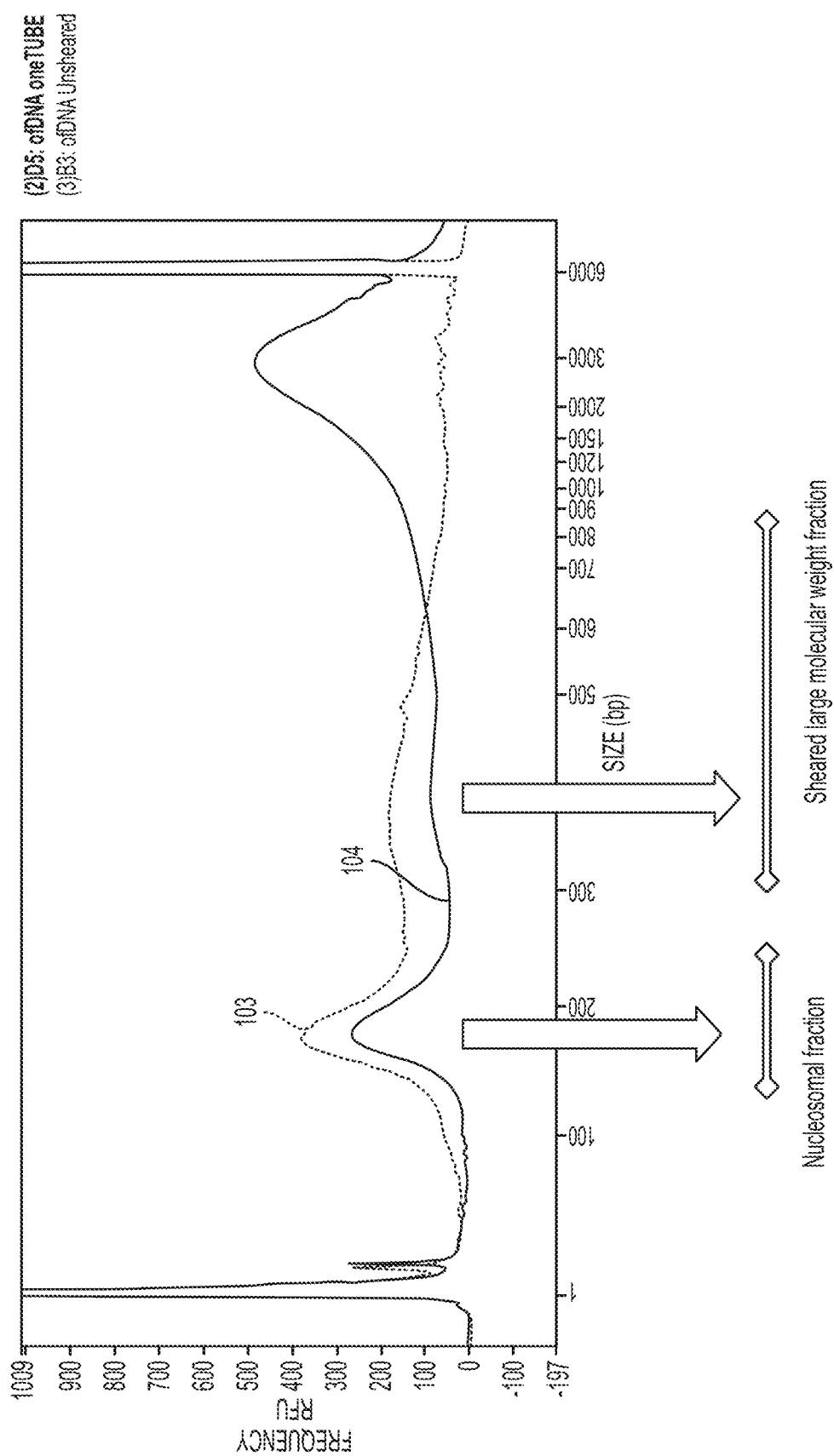
FIG. 2 shows a schematic representation of the sequence analysis of two multiplexed fragment size pools present in a same sample and their distinction by paired end sequencing.

FIG. 2 shows a conceptual illustration of a sample including both small, nucleosomal cfDNA and higher molecular weight cfDNA both before and after treatment with focused acoustic energy. Such treatment shears the higher molecular weight cfDNA fraction from fragment sizes greater than 1000 bp, e.g., 1000 bp to 6000 bp, to a smaller size suitable for NGS analysis, e.g., from 300-500 bp. Importantly, small cfDNA is not affected by the focused acoustic shearing operation. In FIG. 2, the curve 104 shows a cfDNA fragment distribution in a sample, e.g., obtained from a blood sample. As can be seen, the sample includes smaller nucleosomal cfDNA portions having a base pair length of about 180 bp, and higher molecular weight cfDNA portions having a base pair length of about 3000 bp. The curve 103 shows the cfDNA fragment distribution after focused acoustic treatment having a suitable input energy, and illustrates that the higher molecular weight cfDNA portion is sheared to fragments in the range of 300-500 bp and that the smaller cfDNA portion is unaffected. When a NGS library that includes two such different linkerized DNA fragment pools is analyzed, the origins of the sequence information can be deduced simply by the size of the resulting fragments. A typical Illumina paired-end sequence read-out is about 150 bp long. Thus, any fragments that derived from the naturally occurring nucleosomal (160-180 bp long) cfDNA pool will have almost complete coverage. In contrast, the sheared 300-500 bp fragments that would be derived from the high molecular weight cfDNA fraction that is often present in plasma from healthy and frequently present in plasma from cancer patients will not result in paired end reads and can thus be distinguished from the nucleosomal cfDNA fraction, provided that they contain pathology-related sequence mutations. Thus, allele frequency differences in an assembled double-stranded sequence covered fragment and that of a single, non-paired read can be evaluated.

In some experiments described below, bacteriophage Lambda DNA was sheared to a mean fragment size of about 2.99 kb, and this sheared DNA was used to mimic a high molecular weight cfDNA fraction that may be found in cfDNA isolates from certain individuals such as those with certain types of cancers. Specifically, to prepare the sheared 2.99 kb DNA fragments, bacteriophage Lambda DNA (4 ng/µl in TE buffer) was sheared to a target mean size of 3 kb in a Covaris miniTUBE blue using a Covaris M220 focused ultrasonicator. 2 µl of the resulting sheared 2.99 kb DNA was analyzed via Fragment Analyzer (Advanced Analytical Technologies, Ankeny, Iowa) using the HS NGS Kit. Based on the resulting electropherogram shown in FIG. 3, the Lambda DNA was determined to have been sheared to a mean fragment size of 2.99 kb.

Figure 3:
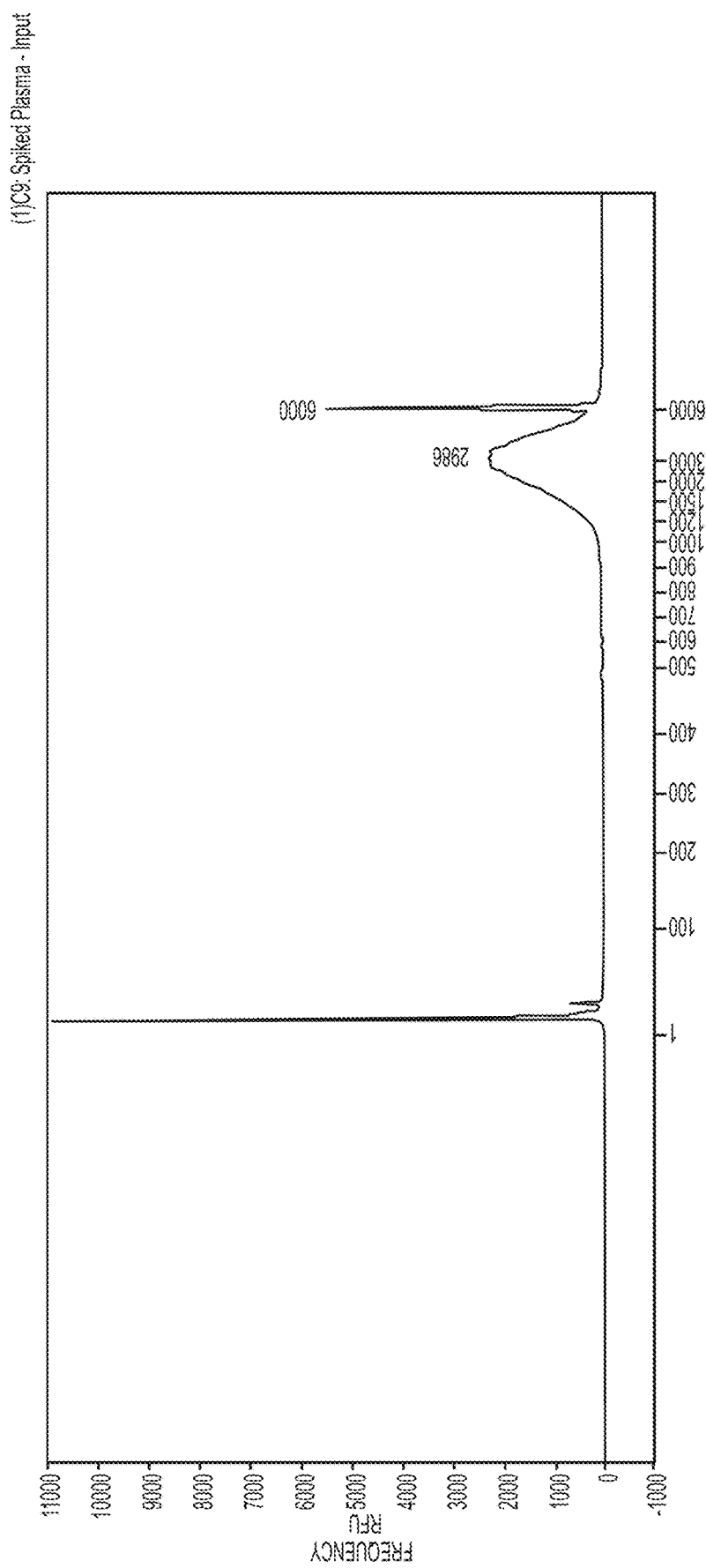
FIG. 3 shows Lambda DNA that was sheared to a target size distribution of 3 kb in one embodiment for use in spiking samples.

In one example intended to determine whether shorter DNA fragments (such as nucleosomal cfDNA) is affected by focused acoustic shearing of larger DNA fragments in a comingled sample, the sheared 2.99 kbp DNA from FIG. 3 was spiked into platelet-depleted human plasma. Initially, the plasma was collected from a healthy subject and prepared using Streck BCT's according to the manufacturer's protocol. (https://www.streck.com/resources/Cell_Stabilization/Cell-Free_DNA_BCT/01_Instructions_(IFU)/01_IFU_Cell-Free_DNA_BCT_IFU.pdf) (Streck, Omaha, Nebr.). 0.9 mL of the plasma was spiked with 20 ng of sheared Lambda DNA from FIG. 3 and then processed according to Covaris truXTRAC-cfDNA from Plasma kit (P/N 520234; Covaris, Woburn, Mass.). In brief, per 0.9 mL platelet-depleted plasma, 40 µl of Proteinase K (20 mg/mL), 24 µl of Conditioning Buffer and 5 µl of 4 ng/µl sheared Lambda DNA (Mean size distribution=2.99 kb) was mixed in a miniTUBE-1 ml (Covaris) and treated with focused acoustic energy in a M220 instrument at 20° C. Focused acoustic energy parameters for the M220 were set as follows: 100 Watts (PIP), 10% Duty Factor, 200 Cycles per Burst for varying amounts of time, i.e., 1 minute, 5 minutes, 5 minutes 50 seconds and 6 minutes 40 seconds for each of four samples. Note, that the 60 second treatment is the condition that is used per truXTRAC-cfDNA kit protocol, which is not designed to shear cfDNA in plasma, but merely to dislodge it from proteins, apoptotic bodies and other cell debris. The increase in total energy by increasing treatment times 5 fold and higher were intended to shear the higher molecular weight DNA (i.e., the spiked 2.99 kb Lambda DNA) to a target of 300-500 bp. Since the 2.99 kb Lambda DNA fragment pools were present in plasma, focused acoustic energy needed to shear it to 300-500 bp was expected to be higher as compared to the same DNA being present in TE buffer or water. This is due to the density of human plasma and the high protein content which absorbs acoustic energy, thereby reducing the energy available for DNA shearing.

Figure 4:
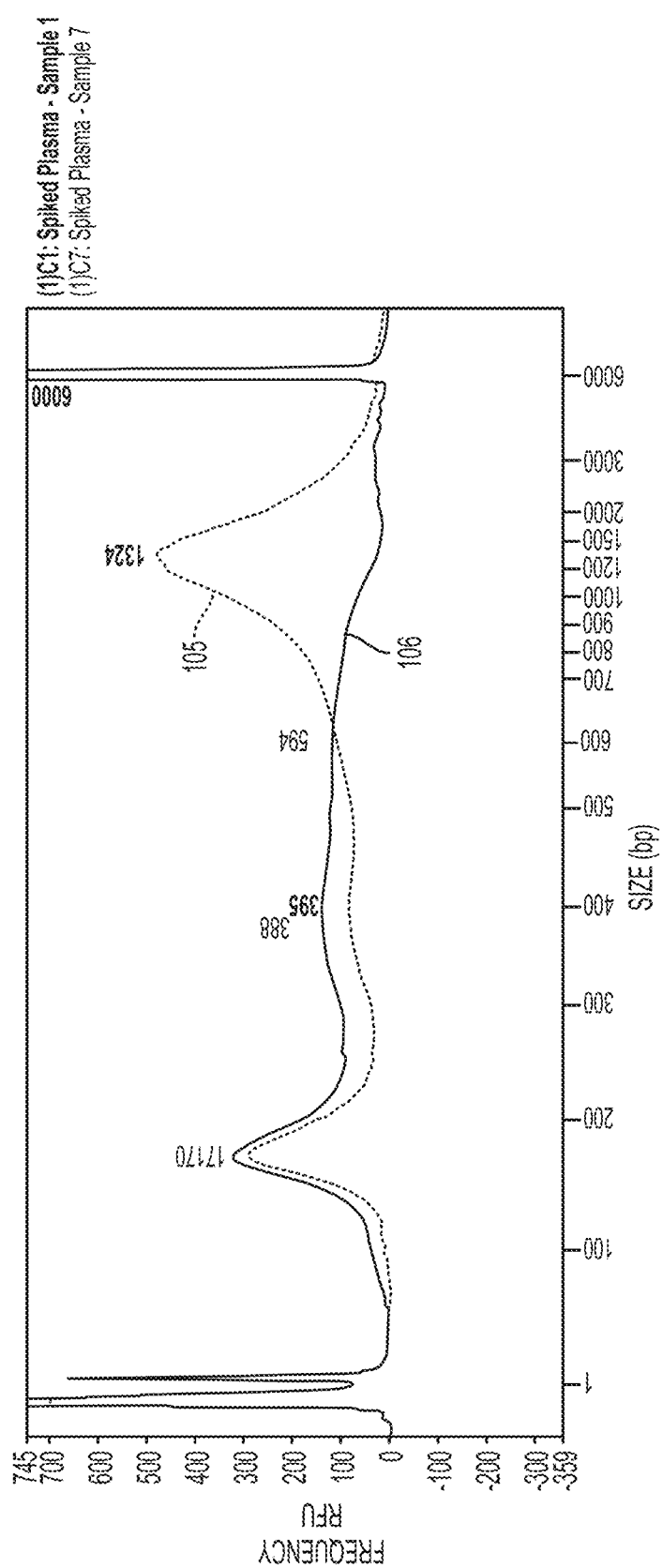
FIG. 4 shows the shearing of the high molecular weight fraction of DNA present in purified cfDNA.

The total energy inputs tested were 600 Joules (normal 1 minute truXTRAC-cfDNA from Plasma kit settings), 3000 (5 minute), 3500 (5 minutes 50 seconds) and 4000 Joules (6 minutes 40 seconds). After focused acoustic treatment, the intrinsic cfDNA and spiked Lambda DNA were purified per truXTRAC-cfDNA protocol. 2 µl of the resulting purified cfDNA/Lambda spiked samples were analyzed via Fragment Analyzer (Advanced Analytical Technologies, Ankeny, Iowa) using the HS NGS Kit, and mean size distributions were determined. The following observations were made from the electropherogram results illustrated in part in FIG. 4, which shows fragment size distributions for the samples treated with 600 Joules total energy (curve 105) and 4000 Joules total energy (curve 106). The nuclesomal fraction of the cfDNA (naturally present in human plasma) was not impacted by the focused acoustic treatment in any of the different treatment energies. For example, curves 105 and 106 illustrate that the fragment distribution for sizes between about 150 bp and 250 bp was not different for the 600 Joule treatment experiment (which was not expected to shear any DNA fragments due to the relatively low total energy) as compared to the 4000 Joule treatment experiment (which was expected to shear DNA fragments about 350 bp). In contrast the spiked 2.99 kbp Lambda DNA decreased in size from 2.99 kb mean to a 1320 bp mean, 1035 bp mean, 911 bp mean and 650 bp mean, respectively for the total energy treatments of 600 Joules, 3000 Joules, 3500 Joules and 4000 Joules. (Note that the resulting mean fragment sizes for the spiked 2.99 kbp Lambda DNA do not match those in FIG. 1. This is, in part, because of the presence of human plasma rather than TE buffer for the shows shearing of high molecular weight DNA in presence of a sheared population of low molecular weight DNA fragments in one embodiment results in FIG. 1.)

Figure 5:
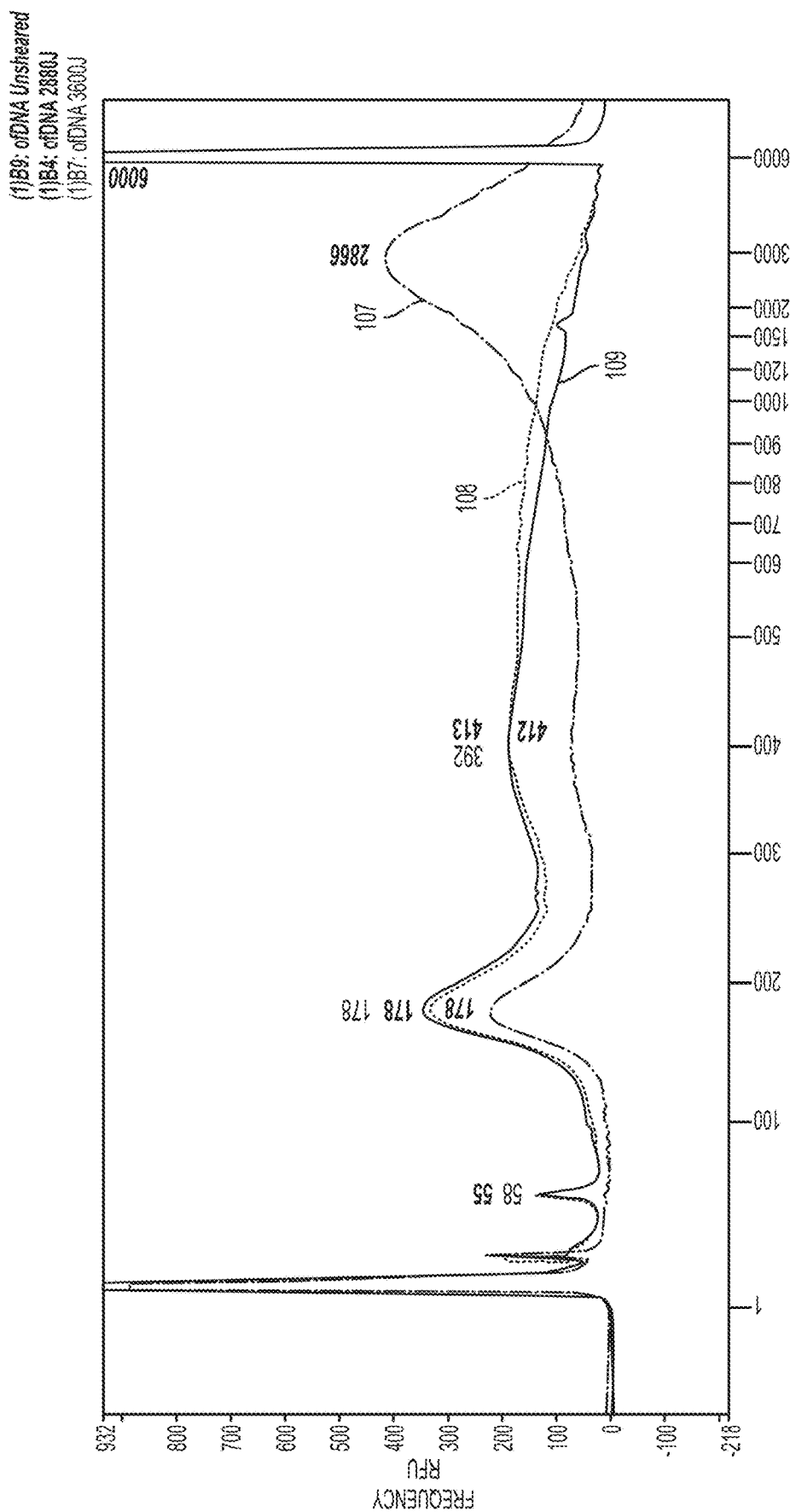
FIG. 5 shows shearing of high molecular weight DNA that was spiked into isolated human cfDNA in one embodiment.

In another example intended to determine whether shorter DNA fragments (such as nucleosomal cfDNA) are affected by focused acoustic shearing of larger DNA fragments in a comingled sample, plasma from a healthy donor that contains a high proportion of high molecular weight cfDNA, and that was previously stored frozen, was used. This experiment was intended to demonstrate differential shearing of the high molecular weight fraction without impacting the nucleosomal small 170 bp cfDNA fraction that was present in the sample. 0.9 mL of the platelet-depleted plasma was mixed with 40 µl of Proteinase K (20 mg/mL), 24 µl of Conditioning Buffer and subjected to focused acoustic treatment in a Covaris E220 Focused-ultrasonicator. Settings for the E220 were 100 Watts (PIP), 10% Duty Factor and 200 Cycles per Burst for a total energy of 600 Joules, 2880 Joules and 3600 Joules for each of three different samples. cfDNA in the treated plasma was then isolated using Covaris truXTRAC-cfDNA from Plasma kit (P/N 520234; Covaris, Woburn, Mass.). All samples were analyzed via Fragment Analyzer as described above, and the electropherograms shown in FIG. 5 used to determine the mean fragment sizes. At 600 Joules, the high molecular weight cfDNA was sheared to a mean fragment size of 2870 bp as shown in curve 107 in FIG. 5. Applying more total energy (2880 Joules) moved this fraction to a mean size of 410 bp (curve 108) and treatment with 3600 Joules resulted in a mean base pair size of 390 bp (curve 109). In all cases, the nucleosomal fraction of the cfDNA (170 bp mean size) was not affected, i.e., was not sheared to smaller fragments.

Figure 6:
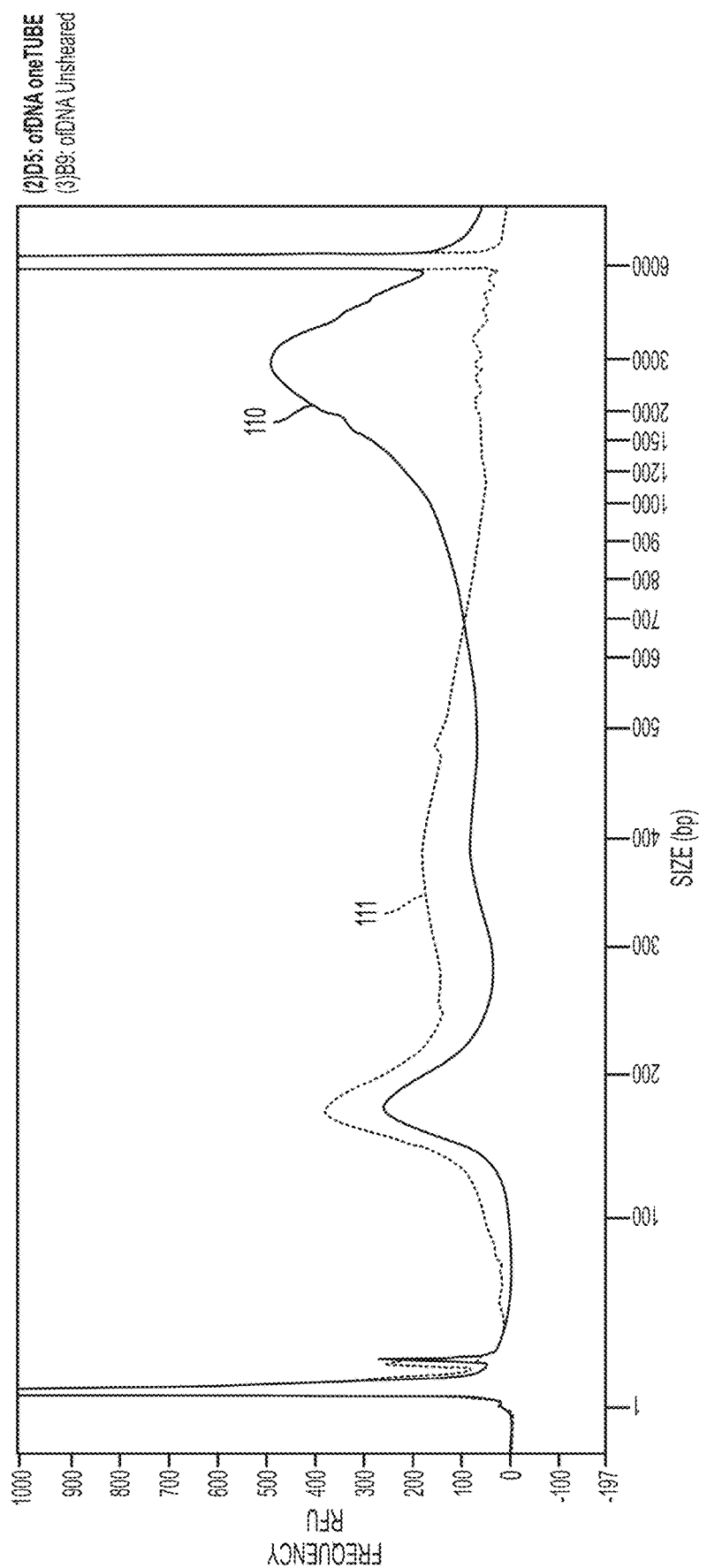
FIG. 6 shows shearing of the high molecular weight fraction of cfDNA present in human plasma.

In another example, cfDNA that was purified following the truXTRAC-cfDNA from Plasma kit protocol was subjected to differential shearing using focused acoustic energy. When isolating cfDNA with the truXTRAC-cfDNA protocol, any large cfDNA fragments are present in a wide size range above 1500 bp. Curve 110 in FIG. 6 shows a typical profile of cfDNA from blood plasma that contains large quantities of the high molecular weight cfDNA fraction (here 2866 bp mean size) in addition to the mono-nucleosomal (178 bp mean size) and di-nucleosomal (about 350 bp mean size) fractions. 10 µl of purified cfDNA that was obtained as described in connection with FIG. 5, and after treating the plasma with 600 Joules of focused acoustic energy as described in the protocol for the Covaris truX-TRAC-cfDNA from Plasma kit, the sample was subjected to 3600 Joules of focused acoustic energy in a Covaris one-TUBE-10 in a E220 focused-ultrasonicator. Settings for the E220 were 200 Watts (PIP), 30% Duty Factor, 200 Cycles per Burst. Samples before and after the high energy post-purification focused acoustic energy treatment were then analyzed via Fragment Analyzer as described above, and the electropherograms used to determine the mean fragment sizes. Curve 111 in FIG. 6 shows the additional fragmenting of the high molecular fragment pool (about 3 kb) present in the sample towards a fragment pool with a mean size of about 380 bp. The nucleosomal fraction (about 170 bp mean size) is not affected by the fragmentation of the high molecular weight cfDNA fraction.

In another experiment, the general usefulness of applying focused acoustic energy to selectively fragment a high molecular weight DNA in presence of sheared or un-sheared low molecular weight DNA was evaluated. As noted above, such shearing into two defined fragment size pools that can be subjected to NGS analysis simultaneously in the same library prep reaction would be useful for distinguishing fragments that stem from different tissues (e.g., cfDNA and cellular DNA, exosomal and nuclear DNA) and cellular compartments (e.g., organellar and nuclear DNA), since they often co-purify but are distinguishable initially by their average fragment length. An alternative is physical size separation by gelelectrophoresis, size-selective binding and elution, gel filtration, etc.

In two separate Covaris microTUBE-130 vessels, Lambda DNA was sheared in an E220 focused-ultrasonicator to a mean size distribution of 146 bp and 478 bp. Settings for the E220 machine were 175 Watt (PIP), 10% Duty Factor and 200 Cycles per Burst for 430 seconds (146 bp protocol) and 105 Watt (PIP), 5% Duty Factor, 200 Cycles per Burst for 80 seconds (480 bp protocol). Size distribution of the sheared products were verified on an Agilent BioAnalyzer 12000 chip.

The following sheared and unsheared DNA sample populations were prepared:

A. Lambda DNA sheared to a fragment population with a mean of 146 bp only;

B. Lambda DBA sheared to a fragment population mean of 146 bp combined with an equivalent mass of unsheared Lambda DNA (48 kbp);

C. Lambda DNA sheared to a fragment population mean of 146 bp combined with an equivalent mass of Lambda DNA sheared to a mean of 480 bp;

D. Lambda DNA sheared to a fragment population mean of 480 bp only.

Figure 7:
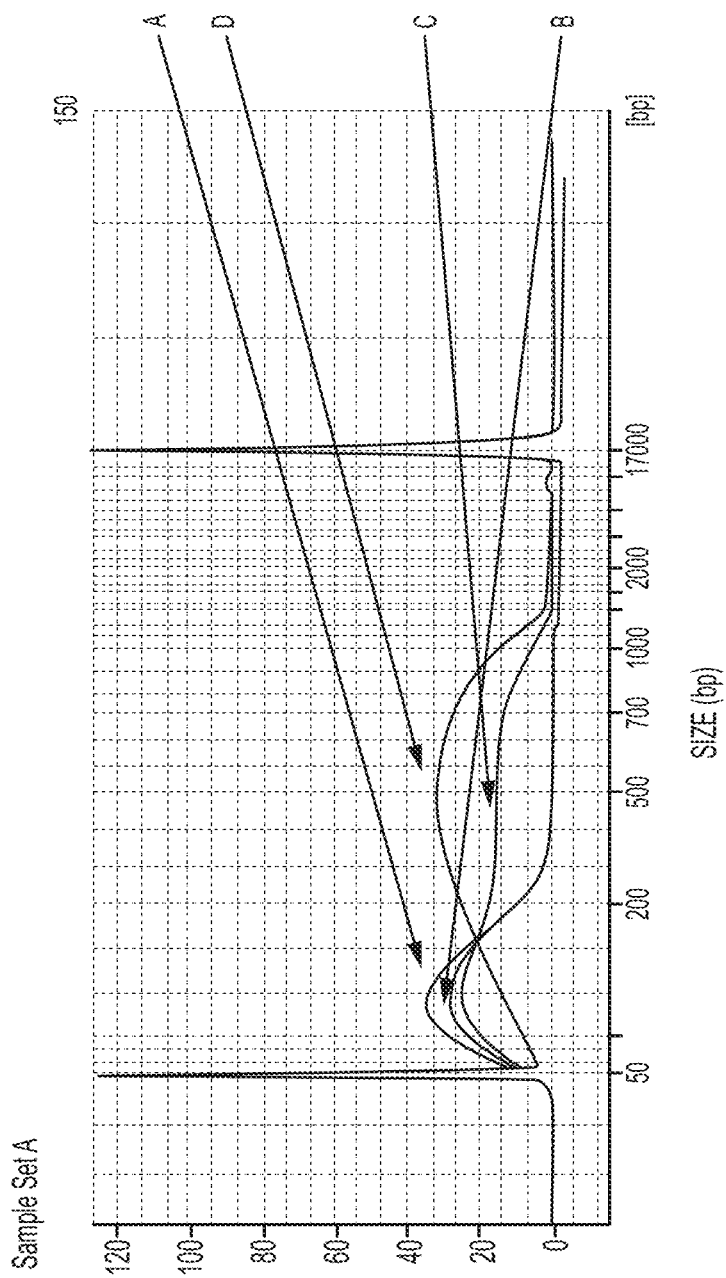
FIG. 7 shows shearing of high molecular weight DNA in presence of a sheared population of low molecular weight DNA fragments in one embodiment.

Prior to size distribution verification, Sample B was subjected to the same focused acoustic energy that was used to fragment unsheared Lambda DNA to the fragment population with a mean of 480 bp in Sample D. Analysis of the fragment size averages obtained after shearing Sample B showed that the unsheared Lambda DNA was sheared to a fragment size population with a mean of 479 bp. The electropherograms of Samples B and C run in triplicate (analysis via a BioAnalyzer 12000 chip/kit as described above) are shown in FIG. 7 and are nearly identical. This shows that at the focused acoustic energy settings for shearing Lambda DNA to an average size of 480 bp in Sample B were not sufficient to fragment the 146 bp fragment pool present in Sample B.

FIG. 8 shows a schematic block diagram of an acoustic treatment system 100 that may be used to provide focused acoustic treatment in one or more embodiments. It should be understood that although embodiments described herein may include most or all aspects of the invention, aspects of the invention may be used alone or in any suitable combination with other aspects of the invention. In this illustrative embodiment, the acoustic treatment system 100 includes an acoustic energy source with an acoustic transducer 14 (e.g., including one or more piezoelectric elements) that is capable of generating an acoustic field (e.g., at a focal zone 17) suitable to cause mixing, e.g., caused by cavitation, and/or other effects in a sample 1 contained in a vessel 4. The sample 1 may include "solid" particles, such as cells, or other material 2, such as cell-free DNA or other nucleic acid material, and/or liquid 3, such as blood serum, water, etc. Under the control of a control circuit 10 (described in more detail below), the acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 8. U.S. Pat. Nos. 6,948,843 and 6,719,449 are incorporated by reference herein for details regarding the construction and operation of an acoustic transducer and its control. The focal zone may be stationary relative to the sample, or it may move relative to the sample.

In some embodiments, the transducer can be formed of a piezoelectric material, such as a piezoelectric ceramic. The ceramic may be fabricated as a "dome", which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing or undamped to increase power output. The response may be linear if not overdriven. The high-energy focus zone 17 of one of these domes is typically cigar-shaped. At 1 MHz, the focal zone 17 is about 6 cm long and about 2 cm wide for a 20 cm dome, or about 15 mm long and about 3 mm wide for a 10 cm dome. The peak positive pressure obtained from such systems at the focal zone 17 is about 1 MPa (mega Pascal) to about 10 MPa pressure, or about 150 PSI (pounds per square inch) to about 1500 PSI, depending on the driving voltage. The focal zone 17, defined as having an acoustic intensity within about 6 dB of the peak acoustic intensity, is formed around the geometric focal point. It is also possible to generate a line-shaped focal zone, e.g., that spans the width of a multi-well plate and enables the system 1 to treat multiple wells simultaneously.

To control an acoustic transducer 14, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. Moreover, the system control circuit 10 may control various other acoustic treatment system 100 functions, such as positioning of the vessel 4 and/or acoustic transducer 14, receiving operator input (such as commands for system operation), outputting information (e.g., to a visible display screen, indicator lights, sample treatment status information in electronic data form, and so on), and others. Thus, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

The vessel 4 may have any suitable size or other arrangement, e.g., may be a glass or metal tube, a plastic container, a well in a microtiter plate, a vial, or other, and may be supported at a location by a vessel holder 12. Although a vessel holder 12 is not necessarily required, the vessel holder 12 may interface with the control circuit 10 so that the vessel 4 and the sample in the vessel is positioned in a known location relative to an acoustic field, for example, at least partially within a focal zone of acoustic energy. In this embodiment, the vessel 4 is a borosilicate glass tube, but it should be understood that the vessel 4 may have other suitable shapes, sizes, materials, or other feature, as discussed more below. For example, the vessel 4 may be a cylindrical tube with a flat bottom and a threaded top end to receive a cap, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

The invention claimed is:

1. A method for shearing selected nucleic acid portions of a sample, comprising:
   providing a sample in a vessel containing a first set of nucleic acid portions having a first base pair length and a second set of nucleic acid portions having a second base pair length, the second base pair length being larger than the first base pair length; and
   exposing the sample in the vessel, having both the first set and second set of nucleic acid portions, to focused acoustic energy to selectively shear only the second set of nucleic acid portions to produce a third set of nucleic acid portions having a third base pair length that is less than the second base pair length but greater than the first base pair length, the focused acoustic energy not shearing the first set of nucleic acid portions.

2. The method of claim 1, wherein the sample includes blood having nucleosomal cfDNA comprising the first set of nucleic acid portions and larger base pair length cfDNA comprising the second set of nucleic acid portions.

3. The method of claim 2, wherein the larger base pair length cfDNA is apoptotic or necrotic in origin.

4. The method of claim 2, wherein the nucleosomal cfDNA has a base pair length of less than 180 bp, and the larger base pair length cfDNA has a base pair length greater than 1000 bp.

5. The method of claim 2, wherein the nucleosomal cfDNA has a base pair length of less than 400 bp, and the larger base pair length cfDNA has a base pair length greater than 500 bp.

6. The method of claim 2, wherein the third set of nucleic acid portions includes sheared fragments of the larger base pair length cfDNA, wherein the sheared fragments have a base pair length of about 300-500 bp.

7. The method of claim 1, further comprising:
simultaneously using the first and third sets of nucleic acid portions together in a library of a next generation sequencing (NGS) process.

8. The method of claim 1, further comprising:
separating the first and third sets of nucleic acid portions by gel electrophoresis, size-selective binding and elution or gel filtration.

9. The method of claim 1, wherein the focused acoustic energy has a duty cycle of 50% or less, and a peak incident power (PIP) of 20 W to 200 W.

10. The method of claim 1, wherein the focused acoustic energy is generated by an acoustic energy source spaced from and exterior to the vessel, and the focused acoustic energy comprises a frequency of between about 100 kilohertz and about 100 megahertz and a focal zone having a width of less than about 2 centimeters.

11. The method of claim 10, wherein the acoustic energy source includes an acoustic transducer having a dome shape and arranged to generate focused acoustic energy to create the focal zone.

12. The method of claim 1, wherein the sample has a volume of 10 microliters to 150 milliliters.

13. The method of claim 1, wherein the step of exposing the sample includes controlling the focused acoustic energy to provide a total input energy to the sample to shear only the second set of nucleic acid portions to a minimum base pair length that corresponds to the total input energy and that is greater than the first base pair length.

14. A method for shearing selected nucleic acid portions of a sample, comprising:
providing a sample in a vessel containing a first set of nucleic acid portions including supercoiled DNA having a first base pair length and a second set of nucleic acid portions including linear DNA having a second base pair length; and
exposing the sample in the vessel, having both the first set and second set of nucleic acid portions, to focused acoustic energy to selectively shear only the second set of nucleic acid portions to produce a third set of nucleic acid portions having a third base pair length that is less than the second base pair length of the second set of nucleic acid portions, the focused acoustic energy not shearing the first set of nucleic acid portions.

15. A method for shearing selected nucleic acid portions of a sample, comprising:
providing a sample in a vessel containing a first set of nucleic acid portions each having a base pair length less than a threshold and a second set of nucleic acid portions each having a base pair length greater than the threshold; and
exposing the sample in the vessel, having both the first set and second set of nucleic acid portions, to focused acoustic energy to selectively shear only the second set of nucleic acid portions to produce a third set of nucleic acid portions having a base pair length that is less than the base pair length of the second set of nucleic acid portions but greater than the base pair length of the first set of nucleic acid portions, the focused acoustic energy not shearing the first set of nucleic acid portions.

16. The method of claim 14, wherein the step of exposing the sample includes controlling the focused acoustic energy to provide a total input energy to the sample to shear only the second set of nucleic acid portions to a minimum base pair length that is greater than the threshold.

* * * * *